US005514139A

United States Patent [19]
Goldstein et al.

[11] Patent Number: 5,514,139
[45] Date of Patent: May 7, 1996

[54] METHOD AND APPARATUS FOR FEMORAL RESECTION

[75] Inventors: David B. Goldstein; Timothy Haines, both of Hoboken, N.J.

[73] Assignee: Hudson Surgical Design, Inc., Stewartsville, N.J.

[21] Appl. No.: 300,379

[22] Filed: Sep. 2, 1994

[51] Int. Cl.$^6$ ................................................ A61B 17/56
[52] U.S. Cl. ....................................... 606/79; 606/88
[58] Field of Search ............................ 606/88, 89, 87, 606/86, 80, 82, 96, 97, 98, 79

[56] References Cited

U.S. PATENT DOCUMENTS

| | | |
|---|---|---|
| 4,457,307 | 7/1984 | Stillwell . |
| 4,474,177 | 10/1984 | Whiteside ............................ 606/88 X |
| 4,566,448 | 1/1986 | Rohr, Jr. . |
| 4,586,496 | 5/1986 | Keller . |
| 4,721,104 | 1/1988 | Kaufman et al. . |
| 4,722,330 | 2/1988 | Russell et al. . |
| 4,787,383 | 11/1988 | Kenna . |
| 4,892,093 | 1/1990 | Zarnowski et al. ..................... 606/82 |
| 4,896,663 | 1/1990 | Vandewalls ............................ 606/79 |
| 5,047,032 | 9/1991 | Jellicoe ................................ 606/83 |
| 5,049,149 | 9/1991 | Schmidt .............................. 606/87 |
| 5,053,037 | 10/1991 | Lackey ................................ 606/79 |
| 5,098,436 | 3/1992 | Ferrante et al. ......................... 606/88 |
| 5,234,432 | 8/1993 | Brown ................................ 606/79 |
| 5,234,433 | 8/1993 | Bert et al. ............................ 606/88 |

FOREIGN PATENT DOCUMENTS

| | | |
|---|---|---|
| 466659 | 1/1992 | European Pat. Off. . |
| 538153 | 4/1993 | European Pat. Off. . |
| 577020 | 10/1977 | U.S.S.R. .............................. 606/88 |

*Primary Examiner*—Guy Tucker
*Attorney, Agent, or Firm*—Friscia & Nussbaum

[57] ABSTRACT

A distal femur resecting apparatus for use in the preparation of a human distal femur for the implantation of a human femoral prosthesis. The resecting apparatus includes a positioning apparatus and a pattern device. The positioning apparatus includes a positioning block for attachment to a femur, an adjustment block having an intermedullary rod extending into the femur, and a rotational alignment device for attachment of the pattern device to the positioning apparatus. The pattern device comprises an individual or pair of mediolaterally located plates having a cutting path described therethrough similar in shape to the interior profile of a human femoral prosthesis. The cutting path guides a reciprocating, oscillating, or rotating cutting tool along a path for removing material from some or all of the distal femur to shape the distal femur to accept a distal femoral prosthesis.

19 Claims, 6 Drawing Sheets

METHOD AND APPARATUS FOR FEMORAL RESECTION

BACKGROUND OF THE INVENTION

1. Field of the Invention

This invention generally relates to a method and apparatus to resect the distal human femur to allow it to properly accept a distal femoral prosthesis.

2. Description of the Prior Art

Different methods and apparatus have been developed to enable a surgeon to resect the distal human femur to allow attachment of a distal femoral prosthesis (knee implant) to the human femur. Keeping in mind the ultimate goal of the procedure is to restore the knee joint to normal function, it is critical that the location and orientation of the knee implant approximates that of the natural knee.

It is common to use the central axis of the femur, the posterior and distal femoral condyles, and/or the anterior distal femoral cortex as guides to determine the location and orientation of distal femoral resections. The location and orientation of these resections are critical in that they dictate the final location and orientation of the distal femoral implant. It is commonly thought that the location and orientation of the distal femoral implant are critical factors in the success or failure of the artificial knee joint.

Past efforts have not been successful in consistently properly locating and orienting distal femoral resections. Such efforts are set forth in the following patents, none of which teach or suggest all of the benefits and advantages of the present invention. These previous patents include:

Stillwell, U.S. Pat. No. 4,457,307, which discloses a movable saw and saw carriage which may be mounted to a patient's femur and positioned to cut the femur bone. An elongated rail is secured substantially parallel to the femur. A saw carriage and a carriage housing are attached to the rail. The saw has a blade extending substantially parallel to the direction of linear movement of the saw carriage. The saw carriage is slidably guided along paths substantially parallel to the elongated rails for making cuts in the femur bone. The saw may be positioned in a plurality of second positions where the saw carriage is slidably guided in paths substantially perpendicular to the elongated rail for making traverse distal femur cuts and for scoring the tibia cortex. Additionally, the saw may be positioned in a plurality of third positions where the saw carriage is slidably guided to form an acute angle with the elongated rail for making anterior and posterior femur chamfer cuts.

Rohr, U.S. Pat. No. 4,566,448, discloses a ligament tensor device having a first member to engage the tibia and a second member to engage the intercondylar notch of a femur and a means for moving the second means with respect to the first means for applying a selected tension to the ligaments of the joint. Additionally, the invention includes cutting guide slots for guiding the cutting of the femoral condyles.

Keller, U.S. Pat. No. 4,586,496, discloses a surgical chisel having a flexurally rigid chisel shank and a thin, elongated chisel blade fixed at its front end. A chisel guide is provided having slides for displaceably guiding the blade and shank in a longitudinal direction.

Russell et al., U.S. Pat. No. 4,722,330, discloses a distal femoral surface shaping guide for mounting on an intramedullary alignment guide for use in shaping the distal femoral surface. A conventional shaping means such as an oscillating saw or hand saw is introduced through the guide surfaces to resection the femur. The device also includes stabilizing members with threaded, knurled cap bolts with points that extend along the sides of the femur to stabilize the device.

Zarnowski et al., U.S. Pat. No. 4,892,093, discloses a cutting guide for a saw blade for resecting a femur. The device is attached to a femur after the distal end has been removed and a transverse surface has been established. The cutting guide includes a base member having a planar base surface. A pair of laterally spaced-apart locating and securing posts are integral with the base member and project in a direction normal to the base surface to interconnect with the femur. Guide members in the form of cylindrical bars are positioned within side members attached to the base. A saw blade may be inserted between the guide surfaces to properly position the blade to cut the femur.

Vandewalls, U.S. Pat. No. 4,896,663, discloses a drill for drilling a hole into a femur. The device includes a positioning mechanism to firmly engage the outer peripheral surface of the femoral head and the femoral neck. This immobilizes the drill bushing relative to the femur and orients the axis of the drill with the central axis of the femur.

Schmidt, U.S. Pat. No. 5,049,149, discloses a sawing gauge system for intertrochantery accommodation osteotomies for removing a wedge-shaped section of bone with a predetermined wedge-angle so that an optimal pre-stress load F can act.

Lackey, U.S. Pat. No. 5,053,037, discloses a femoral drill guide with interchangeable femoral collets, a femoral reamer and a femoral anterior/posterior cutting block with an adoptable anterior femoral ledge. A plurality of diagonal slots are provided for making diagonal cuts in the distal end of the femur.

Ferrante et al. U.S. Pat. No. 5,098,436, discloses a modular guide for shaping a femur comprising a first bracket defining a generally U-shaped structure having an internal surface adapted to be seated on the distal aspect of a resected femur bone and an elongated central opening appointed to expose a selected area of the resected femur, including a curved track for guiding a first shaping tool along a predetermined path for controlled shaping of a curved patellar groove and a portion of the selected area exposed through the opening. A second bracket defines a linear slotted bore extending generally parallel to the long axis of the femur for guiding a second shaping tool to form a relatively deep recess accommodating an intercondylar-stabilizing housing of a knee implant.

Brown, U.S. Pat. No. 5,234,432, discloses a method of cutting the proximal end of a femur prior to cementing in a prosthesis for reconstructive hip surgery.

Additionally, Whiteside, U.S. Pat. No. 4,474,177 describes instruments for creating the distal femoral surfaces where a guide is used to index a flat surface used to guide the distal femoral resection. Kaufman, et al. U.S. Pat. No. 4,721,104 describes a method of preparing the intracondylar area of the distal femur. In addition, Kenna, U.S. Pat. No. 4,787,383 describes a saw and saw guide used to perform the most distal planar femoral resection. Jellicoe, U.S. Pat. No. 5,047,032 utilizes a side cutting drill to form the distal femoral surface.

None of these previous efforts, however, disclose all of the benefits and advantages of the present invention, nor do these previous patents teach or suggest all of the elements of the present invention.

OBJECTS AND SUMMARY OF THE INVENTION

It is a primary object of the present invention to provide an apparatus for properly resecting the distal human femur.

It is also an object of this invention to provide an apparatus for properly orienting a resection of the distal human femur.

It is an additional object of the resection apparatus of the present invention to properly locate the resection apparatus with respect to the distal human femur.

It is even another object of the resection apparatus of the present invention to properly orient the resection apparatus with respect to the distal human femur.

It is another object of the resection apparatus of the present invention to provide a guide device for establishing the location and orientation of the resection apparatus with respect to the distal human femur.

It is still a further object of the resection apparatus of the present invention to lessen the chances of fatty embolisms.

It is even further object of this invention is to provide a resection apparatus capable of forming some or all of the resected surfaces of the distal human femur.

It is another object of the resection apparatus of the present invention to provide an apparatus which is simple in design and precise and accurate in operation.

It is also an intention of the resection apparatus of the present invention to provide a guide device for determining the location of the long axis of the femur while lessening the chances of fatty embolism.

It is also an object of the resection apparatus of the present invention to provide a device to physically remove material from the distal femur in a pattern dictated by the pattern device.

It is even another object of the resection apparatus of the present invention to provide a circular cutting blade for removing bone from the distal human femur to resection the distal human femur.

It is also an object of the present invention to provide a method for easily and accurately resecting a distal human femur.

These objects and others are met by the resection method and apparatus of the present invention. This apparatus comprises a number of components including a guide device, a pattern device and a cutting device.

The pattern device is oriented and located by the use of the positioning apparatus which references the geometry of the distal femur with respect to the long axis of the femur. Once the positioning apparatus has been properly located, aligned, and initially fixed in place, the pattern device may be attached to the positioning apparatus and subsequently, the pattern device may be rigidly fixed to the distal femur. This ensures the pattern device is properly located and oriented prior to the use of the cutting device to remove material from the distal femur thus dictating the final location and orientation of the distal femoral prosthesis.

More specifically, the positioning apparatus is located and aligned utilizing the intramedullary canal of the femur, (thereby approximating the long axis of the femur). The distal surfaces of the femoral condyles, the anterior surface of the distal femur, and the posterior surfaces will indicate the appropriate locations and orientations of the positioning apparatus. Fixation screws may be used to fix the guide device to the distal femur. The pattern device may then be attached to the positioning apparatus so that the location and orientation of the pattern device matches that of the positioning apparatus. Means may be present in the positioning apparatus and/or pattern device for allowing the following additional adjustments in the location and orientation of the pattern device:

1. internal and external rotational adjustment;
2. varus and valgus angular adjustment;
3. anterior and posterior location adjustment; and
4. proximal and distal location adjustment.

Cannulated screws and fixation nails may then be used to firmly fix the pattern device to the distal femur. The positioning apparatus may then be disconnected from the pattern device and removed from the distal femur. Thus, the location and orientation of the pattern device is established.

The pattern device possesses slot-like features, or a cutting path, having geometry that closely matches the interior profile of the distal femoral prosthesis. The cutting path guides the cutting device through the aforementioned slot-like features to precisely and accurately remove material from the distal femur. Thus the distal femur is thereby properly prepared to accept a properly aligned and located distal prosthesis.

BRIEF DESCRIPTION OF THE DRAWINGS

Other important objects and features of the invention will be apparent from the following detailed description of the invention taken in connection with the accompanying drawings in which.

DETAILED DESCRIPTION OF THE INVENTION

As shown generally in FIGS. 1–6, the resecting apparatus of the present invention comprises a number of components, namely positioning apparatus generally indicated at 10 comprising positioning body generally indicated at 12, angular adjustment block generally indicated at 32, rotational alignment device generally indicated at 50, pattern device generally indicated at 59 and cutting means generally indicated at 90.

Figure 1:
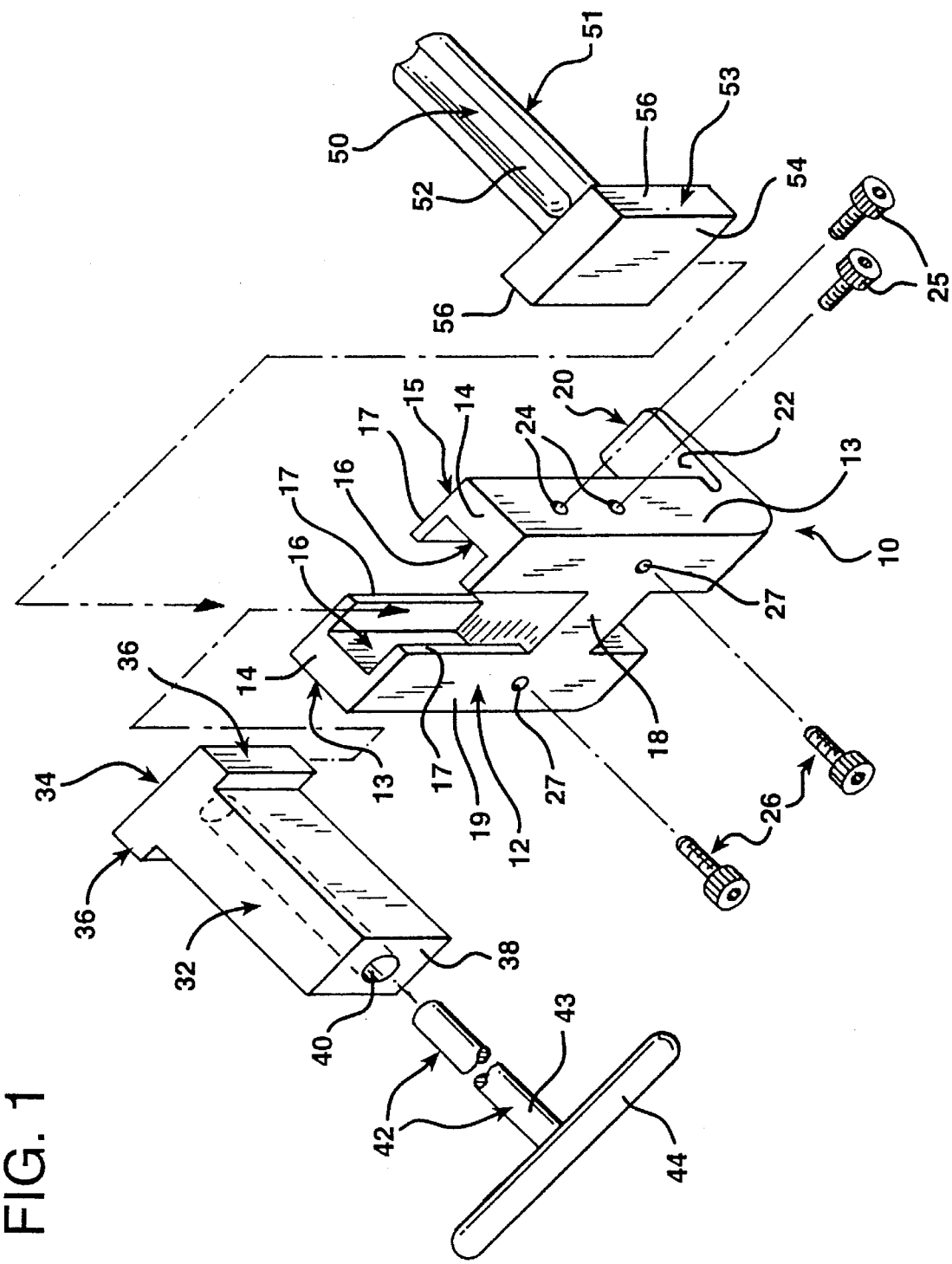
FIG. 1. is an exploded view of the resection apparatus of the present invention showing the positioning apparatus body, the angular adjustment component and the rotational alignment component.

As shown in detail in FIG. 1, the positioning apparatus, generally indicated at 10, includes a positioning body generally indicated at 12 having sides 13, top surface 14, front surface 15, back surface 19 and cross member 18. Extending from a lower end of the positioning body 12 is positioning tongue 20 having an upper surface 22. Extending into the positioning body 12 from top surface 14 to the cross member 18 and through the front and back surfaces 15 and 19, is a gap generally defined by slots 16 and partial slot walls 17. Sides 13 include apertures 24 for receiving locking screws 25. Also extending through the body 12 from the back surface 19 to the front surface 15 are apertures 27 for receiving fixation screws 26.

The positioning apparatus 10 receives and holds angular adjustment block generally indicated at 32. Angular adjustment block 32 includes a front surface 34 having wings 36 sized to be received by the slots 16 in the positioning body 12 to hold the angular adjustment block 32. The angular adjustment block 32 is locked into place in the positioning body 12 by means of locking screws 25 which extend through apertures 24 in the positioning body 12 and contact the wings 36 of the angular adjustment block 32 to secure the angular adjustment block 32 to the positioning body 12. The angular adjustment block 32 establishes the angular alignment and anterior/posterior location of the positioning apparatus 10.

The angular adjustment block 32 also includes back surface 38 and an aperture 40 extending from the back surface 38 through the angular adjustment block 32 to the front surface 34. The aperture 40 receives an intermedullary rod 42 therethrough. The intermedullary rod 42 comprises a shaft 43 and a handle 44. The shaft 43 extends through the angular adjustment block 32 and into the intermedullary canal which extends along the axis of the femur to aid in establishing the orientation of the resection apparatus of the present invention as hereinafter described.

The rotational alignment device, generally indicated at 50, includes a shaft 51 having a groove 52 therealong and a block 53 having a back surface 54 and wings 56. The rotational alignment device 50 is interconnected with the positioning body 12 by means of the wings 56 received in slots 16 of the positioning body 12. The rotational alignment device 50 may be secured to the positioning body 12 by means of locking screws 25 which extend through apertures 24 in the positioning body 12 to contact the wings 56. The locking screws 25 may be made of various configurations depending upon their specific function. Importantly, the locking screws 25 are used to rigidly affix one component or device to another to ensure that the relative locations and orientations are maintained despite the rigors of surgery.

Figure 2:
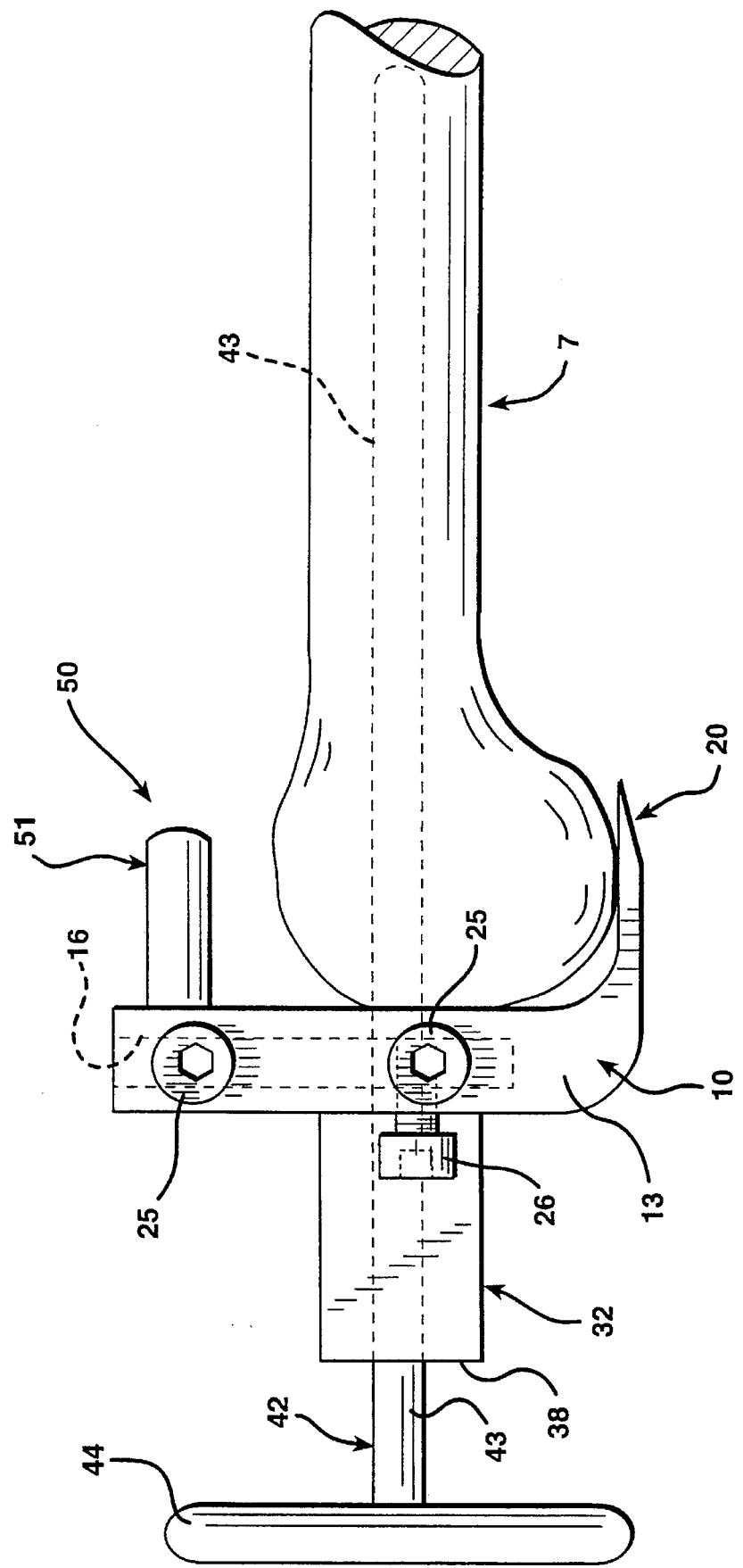
FIG. 2 is a side plan view of the guide device of the resection apparatus of FIG. 1 attached to a distal human femur.
Figure 7:
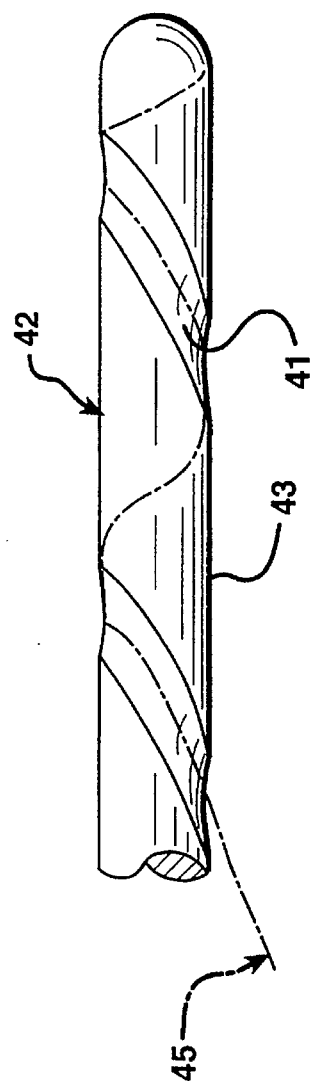
FIG. 7 is a side plan view of an intermedullary rod having a helical groove for use with the resection apparatus shown in FIG. 1.

As shown in FIG. 2, wherein the positioning body 12 is fitted with the angular adjustment block 32 and the rotational alignment device 50, the entire positioning apparatus 10 is connected to a human femur 7 by means of the shaft 43 of the intermedullary rod 42. The shaft 43 extends through the angular adjustment block 32, and thereby through the positioning body 12 into the intermedullary canal which extends along the axis of the femur 7. The intermedullary rod 42, shown in FIG. 7, has a groove 41 transversing a helical path 45 along the axis of the shaft 43. The groove 41 relieves intermedullary pressure that leads to fatty embolisms. The basic concept of the intermedullary rod 42 with the groove 41, is that as it is inserted into the femur, which contains liquid fatty tissue, the liquid fatty tissue is drawn up the groove 41 of the intermedullary rod 42 to draw the fatty liquid tissue out of the femur. Preferably, the intermedullary rod would have a hexagonal head, (not shown) to permit it to be driven by a powered device such as an electrical hand held tool. Importantly, the groove 41 does not have a cutting edge, which would risk perforation of the femoral cortex. Accordingly, the device does not cut solid material, but removes liquid material from the intermedullary canal. Therefore, the risk of fatty embolism is reduced.

After positioning body 12 is properly located against the femur 7 by means of the intermedullary rod 42 and the angular adjustment block 32, fixation screws 26 may be advanced through the apertures 27 in the positioning body 12 until they make contact with the distal femoral condyles of the femur 7, and are then driven into the distal femoral condyles of the femur 7 to initially affix the positioning apparatus to the distal femur 7. It should be noted that the fixation screws 26 may also be advanced and adjusted to make up for deficiencies in the distal femoral condyles. Accordingly, the positioning body 12 is positioned such that the front surface 15 is put into contact with the distal femoral condyles by direct contact, and the tongue 20 is positioned under the femur 7 and in contact therewith.

As can be seen in FIG. 2, the shaft 51 of the rotational alignment device 50 extends above the femur 7 and allows for rotation of the pattern device 59, hereinafter described, about the distal femur 7. Additionally, the rotational alignment device 50 allows for the anterior/posterior positioning of the pattern device 59 with respect to the femur 7. Importantly, the configurations of the positioning body 12, the angular adjustment block 32 and the rotational alignment device 50 are not limited to the structure set forth herein, but may be of different shapes and may interconnect in different ways. These components may even be formed as a unitary or partially unitary device.

Figure 3:
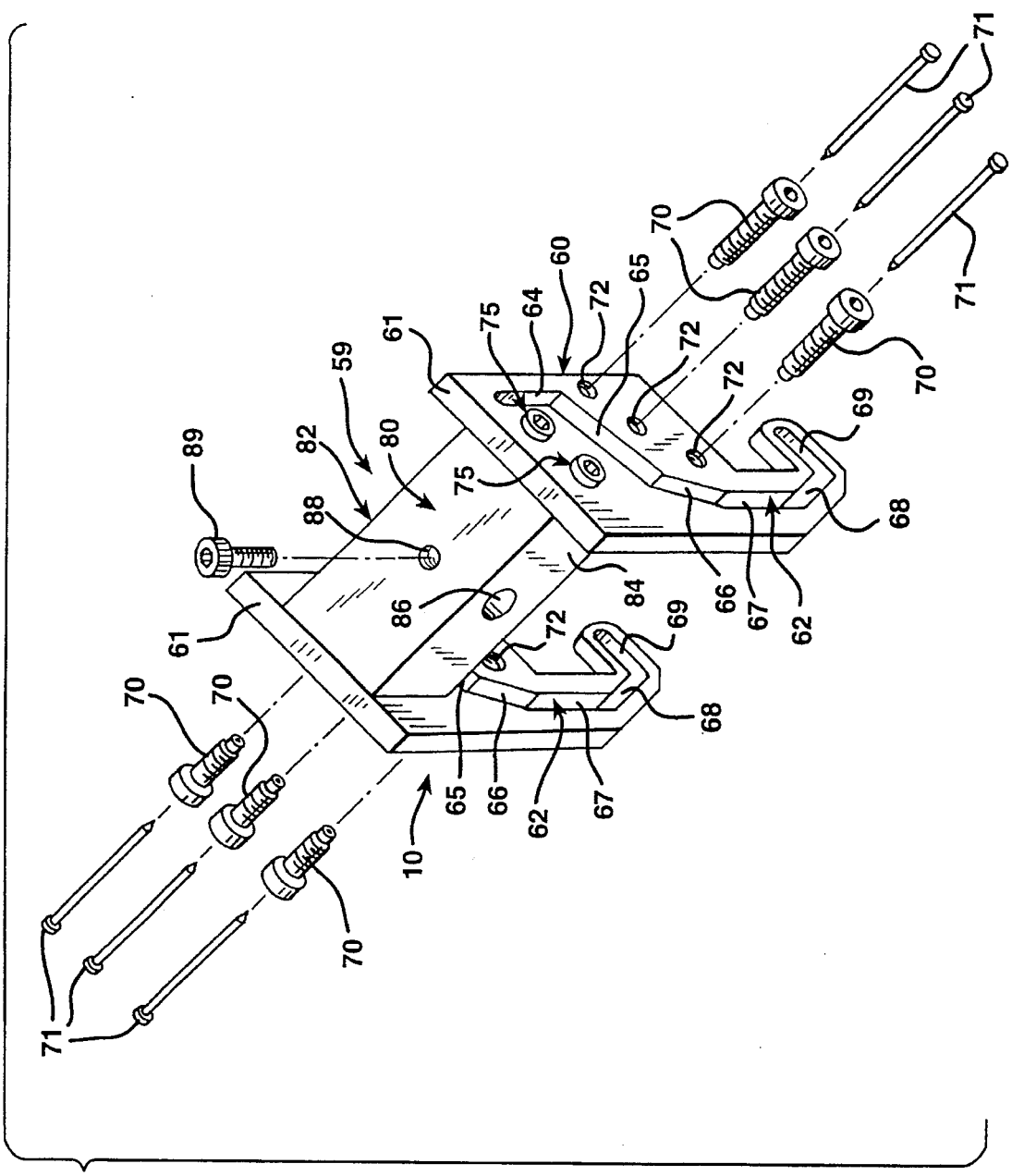
FIG. 3 is an exploded view of the pattern device of the resection apparatus of the present invention.

As shown in FIG. 3, the pattern device 59 includes pattern plates 60 having tops 61, and cutting paths, generally indicated at 62, extending therethrough. The cutting paths 62 outline the desired resection shape of the distal femur 7. Generally, the cutting paths 62 could include a first vertical path 64, extending to a first diagonal path 65, extending to a second diagonal path 66, extending to a second vertical path 67, extending to a third diagonal path 68 and then extending to a horizontal path 69. Alternatively, the cutting paths 62 could describe any desired resection shape for the femur 7. The pattern plates 60 also include locking screws 75 for interconnecting the pattern plates 60 with a crossbar 80.

The pattern device 59 of the present invention preferably includes two pattern plates 60 held in a spaced apart relationship by crossbar 80. The crossbar 80 separates the pattern plates 60 sufficiently to permit the pattern plates 60 to extend along the sides of the distal femur 7. The crossbar 80 includes a front surface 82, back surface 84, a top surface 83, a central aperture 86 extending from the front surface 82 to the back surface 84, a lock aperture 88 extending through the top surface 83, and a lock screw 89. The central aperture 86 of the crossbar 80 receives the shaft 51 of the rotational alignment device 50. Accordingly, the pattern device 59 is interconnected with the positioning apparatus 10 so that the pattern device 59 is properly oriented with respect to the femur 7. Upon proper positioning of the crossbar 80 with respect to the shaft 51 of the rotational alignment device 50, lock screw 89 is extended through lock aperture 88 to contact the shaft 51 to lock the crossbar 80 and, accordingly, the pattern device 59, onto the shaft 51 of the rotational alignment device 50, and accordingly, to positioning apparatus 10. This completed assembly, is attached to the femur 7, is shown in FIG. 4.

Figure 4:
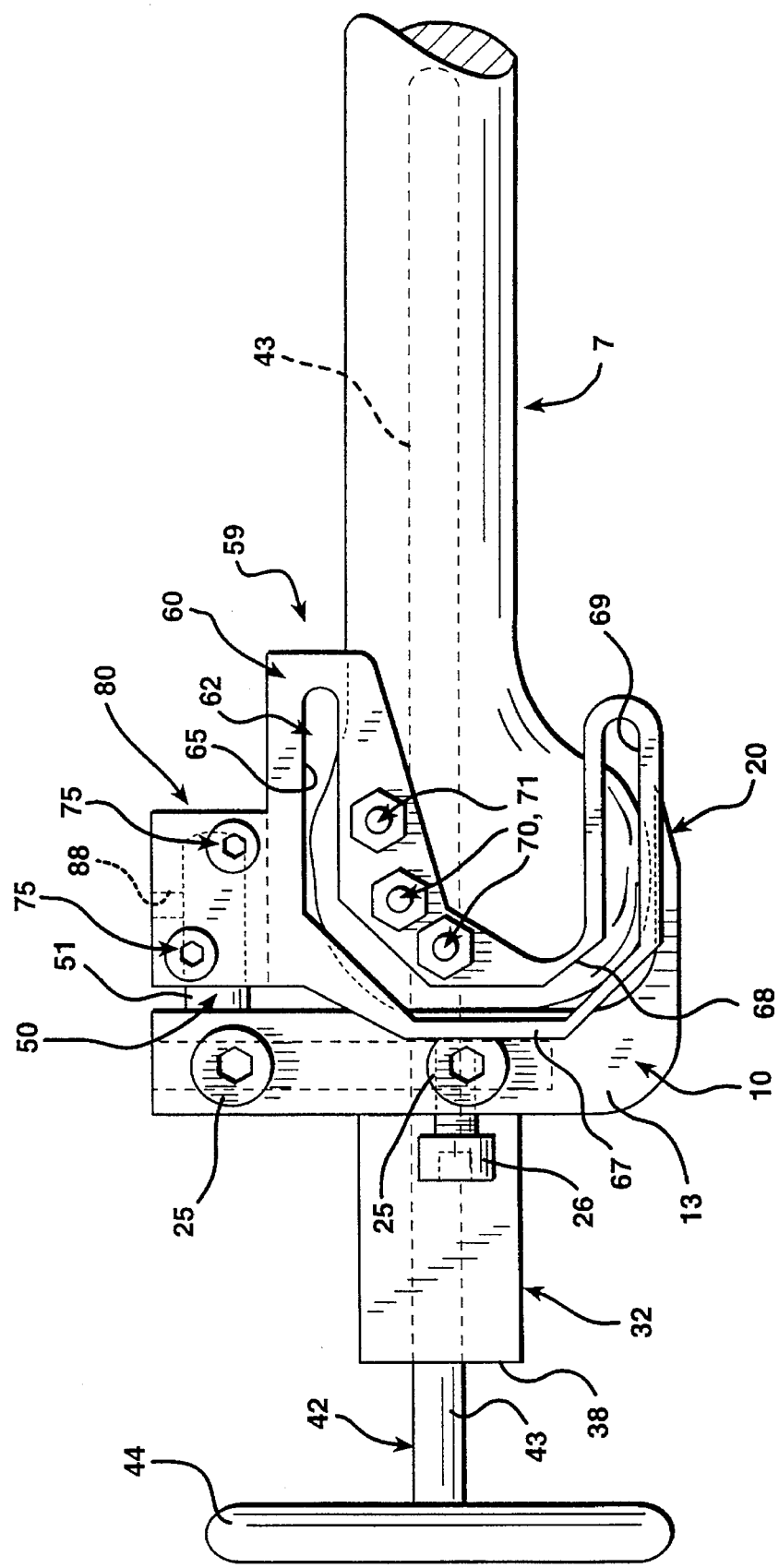
FIG. 4 is a side plan view of the resection apparatus shown in FIG. 2 with the pattern device fixed to the distal human femur.

As additionally shown in FIGS. 3 and 4, the pattern plates 60 include plate apertures 72 for receiving cannulated screws 70 which have apertures extending therethrough for receiving fixation nails 71 therethrough. Accordingly, after the pattern device 59 is interconnected with the positioning apparatus 10, and properly located and oriented with respect to the femur 7, the cannulated screws 70 are extended through the plate aperture 72 to contact the sides of the distal femur 7. Then, in order to fix the pattern plates 60 with respect to the femur 7, the fixation nails 71 are driven into the distal femur 7 to lock the pattern plate 60 into position on the distal femur 7. The cannulated screws 70 have sharp leading edges for allowing decisive purchase in the distal femur 7 before the introduction of the fixation nails 71 to complete fixation of the pattern device 59 to the distal femur 7.

The pattern plates 60 by virtue of the cutting paths 62, dictate the shape of the resection of the femur 7. The cutting paths 62 are essentially channels through the pattern plates 60. The cutting paths 62 receive the cutting device and guide it as it resects the surface of the distal femur 7. The pattern plates 60 straddle the distal femur 7 mediolaterally and are suspended by the crossbar 80. Likewise, the crossbar 80 maintains the proper relationship between the pattern plates 60 before and during the resection of the distal femur 7. The location of the crossbar 80 and accordingly, the pattern plates 60, may be adjusted with respect to the positioning apparatus 10 by adjusting the position of the block 53 of the rotational alignment device 50 within the slots 16 of the positioning body 12, and locking the same with locking screws 25.

Figure 5:
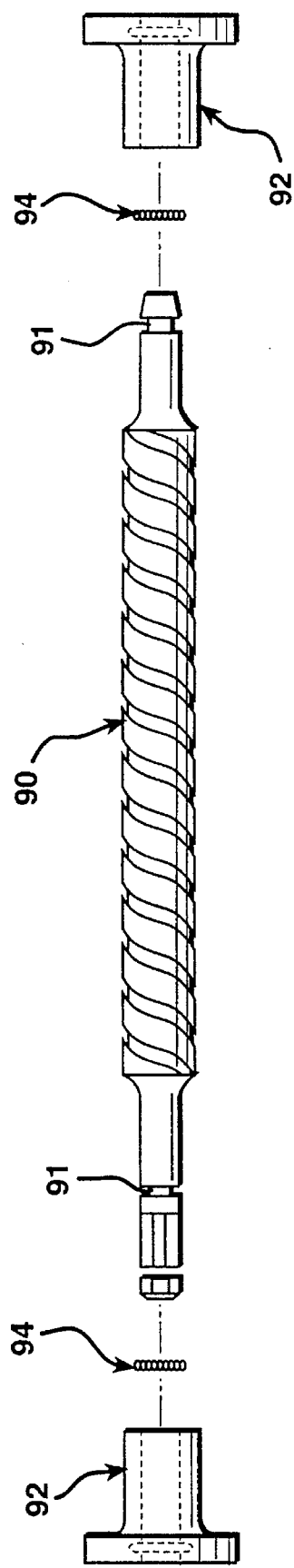
FIG. 5 is an exploded front view of the cutting device of the resection apparatus of the present invention.

The cutting paths 62 in the pattern plates 60 receive and guide the cutting device shown in FIG. 5 and generally indicated at 90. The cutting device 90 performs the actual cutting of the femur 7 to resect the femur 7. The cutting device may be of any known configuration. In a preferred embodiment the cutting device is a drill. The drill 90 is generally cylindrical in shape and may possess helical cutting teeth along its length to cut the femur 7. The drill 90 includes a hexagonal end 95 to permit the use of an electric powered drive, typically an electric drill. Further, the drill 90 includes drill bushings 92 at the ends of the drill 90 to provide a non-metallic bearing between the cutting paths 62 in the pattern plates 60 to avoid galling and to ensure smooth articulation of the drill 90 along the cutting path 62. Positioned between the drill bushings 92 and the drill 90 are retention springs 94 which are essentially coil springs retained within the drill bushings 92 to allow the drill bushings 92 to be easily attached and removed from the drill 90. These retention springs 94 are commercially available in medical grade stainless steels. The drill bushings 92 retain the retention springs 94 which hold the drill bushings 92 in position 92 on the drill 90 while allowing the drill bushings 92 to rotate freely. The drill 90 may also include circumferential grooves 91 for allowing attachment and retention of the drill bushings 92 by means of the retention springs 94. Importantly, the configuration of the drill 90 can vary in accordance with what is known in the art as long, as long as the cutting device can follow the cutting paths 62 in the pattern plates 60 to resect the femur 7.

Figure 6:
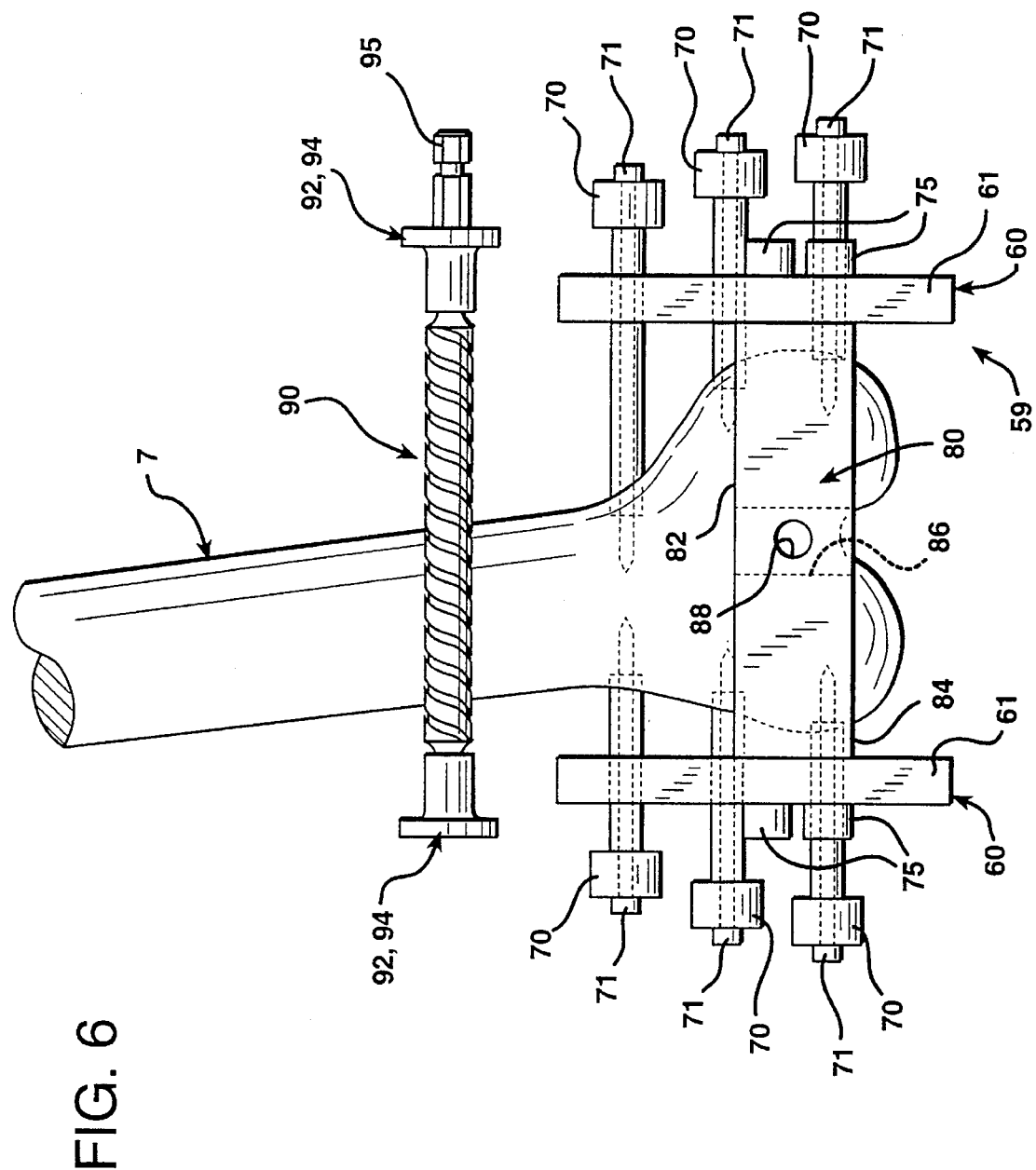
FIG. 6 is a top plan view of the pattern device and the cutting device of the resection apparatus of the present invention affixed to the distal human femur.

As shown in FIG. 6, after the pattern device 59 is attached to the distal femur 7, and positioned accordingly by means of the positioning apparatus 10, and secured to the distal femur 7 by means of cannulated screws 70 and fixation nails 71, positioning apparatus 10 may be removed from connection to the distal femur 7 leaving the pattern device 59 attached to the distal femur 7 to permit resecting of the distal femur. The drill 90 is then positioned within the cutting paths 62 between the pattern plates 60. Next the drill 90 is rotated by power means in connection with the hexagonal end 95, and is then moved along the cutting path 62 to resect the distal femur 7. It should also be noted that the cutting means could be operated by hand.

Instead of two pattern plates 60, a single pattern plate could be employed if it is sufficiently sturdy to support and guide the drill. The pattern plates 60 may also comprise plates having edges in the shape of the desired distal femoral resection pattern. Thus, the cutting device may be drawn along the edges of the pattern plates to resect the distal femur. Further, any cutting device that can be employed to follow the cutting paths in the pattern plates is considered to be within the scope of this invention.

The resection apparatus of the present invention, through proper use as previously described, provides extremely accurate and reproducible bone cuts. While the anterior and distal areas of the femur will almost always be able to be prepared in this manner, interference from soft tissue such as fat and ligaments may prohibit satisfactory preparation of the posterior femur. The preparation of any remaining femoral surfaces may be completed in any manner known in the art after using the instrumentation of the present invention.

Modifications of the foregoing may be made without departing from the spirit and scope of the invention. What is desired to be protected by Letters Patents is set forth in the appended claims.

What is claimed is:

1. A resecting system for resecting a distal human femur for receiving a distal femur prosthesis comprising:

positioning means for positioning a resecting apparatus on a distal human femur, the positioning means having a positioning body comprising:
   a front surface for contacting a human femur;
   a tongue extending from a lower end of the positioning body for extending under a human femur;
   attachment means for attaching the positioning body to a distal human femur;

angular adjustment means for adjusting the angle of the positioning means comprising:
   an adjustment body;
   a rod extendable through the adjustment body and into a distal human femur;
   attachment means for attaching the angular adjustment means to the positioning means;

rotational alignment means comprising:
   an alignment body;
   a shaft extending from the alignment body;
   attachment means for attaching the rotational alignment means to the positioning means;

pattern means for describing a resection pattern comprising:
   opposing pattern plates having cutting paths described therethrough, the cutting paths matching an interior profile of a distal femoral prosthesis;
   support means for supporting the opposing pattern plates;
   attachment means for attaching the support means to the rotational alignment means for rotating the pattern means;
   fixing means for fixing the opposing pattern plates to a side of a distal femur;

cutting means extending through the cutting paths of the pattern means, the cutting means movable along the cutting paths for cutting a distal femur to resect a distal femur.

2. The apparatus of the claim 1 wherein the pattern plates are interconnected by the support means to straddle a distal femur.

3. The apparatus of claim 2 wherein the fixing means for fixing the pattern plates to a distal femur comprises cannulated screws extended through apertures in the pattern plates and fixation nails extendable through the cannulated screws into a distal femur.

4. The apparatus of claim 3 wherein the body of the positioning means further comprises a channel extending into the positioning body from a top surface of the positioning body.

5. The apparatus of claim 4 wherein the body of the angular adjustment means further includes wings sized to be received by the channel in the body of the positioning means.

6. The apparatus of claim 5 wherein the body of the rotational alignment means further includes wings sized to be received by the channel in the body of the positioning means.

7. The apparatus of claim 6 wherein the attachment means for attaching the support means to the rotational alignment means comprises an aperture in the support means for receiving the shaft of the rotational alignment means.

8. The apparatus of claim 7 wherein the cutting means comprises a cylindrical drill and the drill extends through the cutting paths in the pattern plates.

9. A system for resecting a femur comprising:

positioning means for contacting a femur;

support means interconnected with the positioning means;

pattern means interconnected with the support means, the pattern means comprising opposing pattern plates positionable along sides of a femur;

cutting path means described in the pattern plates, the cutting path means matching an interior profile of a distal femoral prosthesis; and cutting means coacting with the cutting path means for cutting a distal femur.

10. The apparatus of claims 9 further comprising an intermedullary rod insertable into a femur, the intermedullary rod interconnected with the positioning means to align the positioning means with respect to a femur.

11. The apparatus of claim 10 wherein the intermedullary rod includes at least one groove extending helically along the length of the intermedullary rod.

12. The apparatus of claim 11 further including an alignment means for receiving the intermedullary rod, the alignment means interconnected with the positioning means.

13. The apparatus of claim 12 wherein the positioning means further comprises a channel extending into the positioning means from an upper surface thereof.

14. The apparatus of claim 13 wherein the alignment means further includes wings sized to be received by the channel in the positioning means.

15. The apparatus of claim 14 wherein the cutting means comprises a cylindrical drill extending through the cutting path means and movable along the cutting path means after the positioning means and the adjustment means are removed from a femur.

16. The apparatus of claim 9 wherein the pattern plates are positionable to straddle a femur.

17. A method for resecting a human femur comprising the steps of:

inserting a rod through an adjustment block into a human femur;

attaching a positioning block to the adjustment block;

affixing the positioning block to a human femur;

interconnecting a rotational alignment device to the positioning block;

interconnecting a support means with the rotational alignment device, the support means supporting pattern plates having cutting paths described therethrough;

positioning the pattern plates along sides of a femur;

affixing the pattern plates to a femur;

removing the positioning block, the alignment device and the adjustment block from the support means;

inserting a cutting means through the cutting paths described in the pattern plates; and tracing the cutting means along the cutting paths described in the pattern plates to resect a femur.

18. The method of claim 17 further comprising the step of employing the adjustment block to adjust the positioning block with respect to a human femur.

19. The method of claim 18 further comprising the step of using the rotational alignment device to align of the support means, and the pattern plates, with the positioning block.

* * * * *